United States Patent
Kantsevoy et al.

(10) Patent No.: US 7,220,253 B2
(45) Date of Patent: May 22, 2007

(54) GASTROJEJUNAL FEEDING TUBE

(75) Inventors: Sergey V. Kantsevoy, Owings Mills, MD (US); Anthony N. Kalloo, Baltimore, MD (US)

(73) Assignee: Chek-Med Systems, Inc., Camp Hill, PA (US)

( * ) Notice: Subject to any disclaimer, the term of this patent is extended or adjusted under 35 U.S.C. 154(b) by 0 days.

(21) Appl. No.: 11/001,846

(22) Filed: Dec. 2, 2004

(65) Prior Publication Data

US 2006/0129124 A1 Jun. 15, 2006

(51) Int. Cl.
*A61M 31/00* (2006.01)
(52) U.S. Cl. .................................................. 604/509
(58) Field of Classification Search ........... 604/103.06, 604/103.07, 523, 910, 264, 45, 43, 103.1, 604/97.02, 96.01, 500, 509, 101
See application file for complete search history.

(56) References Cited

U.S. PATENT DOCUMENTS

| 4,368,739 | A | * | 1/1983 | Nelson, Jr. .................. 604/516 |
| 4,468,739 | A | * | 8/1984 | Woods et al. ................. 701/37 |
| 4,798,592 | A | | 1/1989 | Parks |
| 5,318,530 | A | * | 6/1994 | Nelson, Jr. ............... 604/103.1 |

* cited by examiner

*Primary Examiner*—Nicholas D. Lucchesi
*Assistant Examiner*—Christopher D. Koharski
(74) *Attorney, Agent, or Firm*—Eugene Chovanes

(57) ABSTRACT

An adjustable size balloon at the distal end of a feeding tube is used to aid in positioning, along with an endoscope, the tube in the jejunum or small bowel of a patient, without creating an obstruction in the intestines.

The balloon is fully inflated when the endoscope that is used to place the tube in the duodenum is withdrawn, and then partially deflated to a size that allows peristaltic action on the balloon to move the tube into the jejunum, after which the balloon is further deflated to avoid creating an obstruction in the intestine.

1 Claim, 2 Drawing Sheets

GASTROJEJUNAL FEEDING TUBE

BACKGROUND OF THE INVENTION (1) Field of the Invention

The invention relates to enteral feeding, and more particularly to gastrojejunal feeding.

Specifically, the present invention relates to a feeding tube capable of being placed into the small bowel and anchored with the aid of the natural peristaltic action of the stomach and intestines.

(2) Description of the Prior Art

Feeding tubes, also known as enteral feeding tubes, are widely used in hospitals and nursing homes to provide nourishment to patients that are unable to eat normally.

Various gastrojejunal transnasal or transoral feeding systems of the kind relating to this invention are set forth at length in U.S. Pat. No. 6,458,106, incorporated herein by reference.

In the prior art, percutaneous endoscopic gastrojejunostomy (PEG-J) or direct percutaneous endoscopic jejunostomy (DPEJ) are often performed for patients who cannot tolerate gastric feedings or who are at significant risk for aspiration of gastric feeding solution. Commercially available PEG-J kits use an over-the-wire J-tube method through an existing PEG. These kits allow a 9F to 12F J-tube to be passed through an existing 18F to 28F PEG. After standard PEG placement, the endoscope is reinserted and a guidewire passed through the PEG is grasped in the stomach. The guidewire is advanced with the endoscope into the small intestine. The J-tube is passed over the guidewire into position in the small bowel and plugged into the proximal end of the PEG. Modifications of this technique include maintaining the grasp on the guidewire in the small bowel as the endoscope is withdrawn to help to prevent dislodgment of the J-tube or by using an ultrathin endoscope passed through a 28F PEG tube. The guidewire is fed through the endoscope into position in the small bowel, the endoscope removed, and the J-tube is passed over the wire into the jejunum, where it is the most effective.

Often, however, the feeding tube pulls back into the stomach as the scope is withdrawn and the procedure must be repeated. Notwithstanding such, it is most desirable for the tube to be positioned in the jejunum. Generally, the feeding tube is left in the duodenum with the hope that it will travel on its own into the jejunum. Often, however, the tube migrates back into the stomach instead. Weights have been inserted into the end of the tubes to keep the tube from migrating into the stomach and help with a natural advancement into the jejunum. These do not work well.

The use of a small ball or "bolus" on the end of the feeding tube, as in U.S. Pat. No. 5,057,091, has been tried, but without total success. The art has sought to keep the tube in place in the jejunum after it has been positioned by an endoscope, but often, the tube slips back into the stomach. The fixed bolus is too small to keep the tube in the jejunum.

SUMMARY OF THE PRESENT INVENTION

The present invention uses a balloon capable of being varied in size by inflation and deflation, at the distal end of the feeding tube. First, the balloon is fully inflated after the tube is placed in the duodenum. The fully inflated balloon serves to anchor the feeding tube in the duodenum as the endoscope used to place the tube is withdrawn. The fully inflated balloon prevents the tube from being pulled along with the scope into the stomach.

After removal of the endoscope, the balloon on the end of the feeding tube is then partially deflated to allow duodenal peristalsis carry the balloon and tube into the jejunum. Such placement is difficult to do endoscopically alone.

Since the balloon can be expanded to a much larger size than a fixed size bolus, it is therefore more effective than the prior art. The balloon, by being deflated below its fully expanded state that is necessary for anchoring purposes, avoids the unwanted effect of causing small bowel obstruction by a fixed size balloon or bulus. Most important, the balloon can be adjusted to a size that the body's natural peristaltic action can have effect but kept small enough that it does not cause obstruction.

DESCRIPTION OF THE PREFERRED EMBODIMENT

Figure 1:
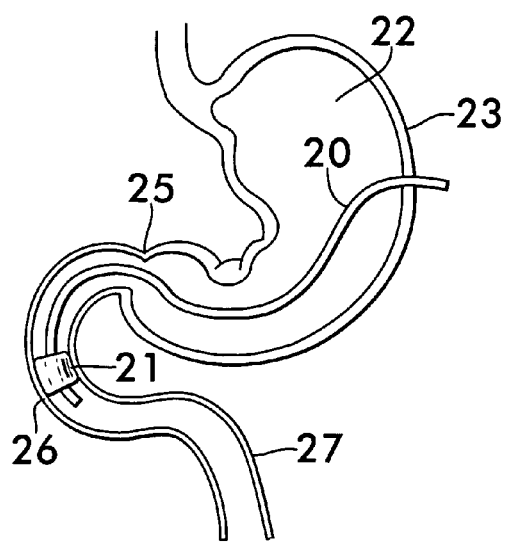
FIG. 1 shows the balloon fully inflated anchoring the feeding tube in the second portion of the duodenum. The tube has been placed through the abdominal wall.

A feeding tube 20, for instance of the type shown in U.S. Pat. No. 4,490,143, incorporated herein by reference, is placed into the position as shown in FIG. 1, using an endoscope in the well-known prior art manner. The feeding tube 20, has at the end thereof an inflatable and deflatable balloon 21 capable of being so inflated and deflated with either air or liquid passed to the balloon through the feeding tube itself during the placement of the tube.

Figure 5:
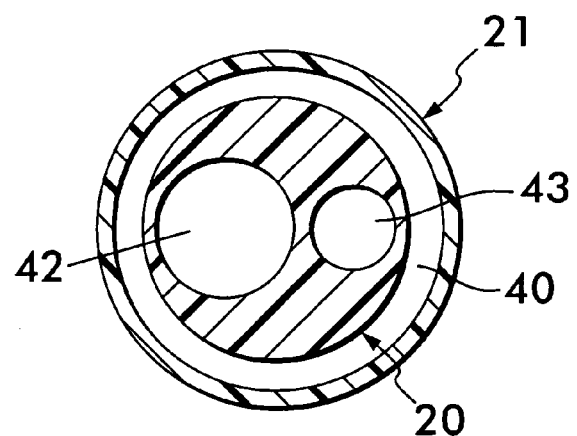
FIG. 5 is a cross section of the feeding tube of FIG. 1 through 3 taken along the tube length above the balloon.

As seen in FIG. 5, the tube 20 has a body 40 containing lumen 42 and lumen 43. Air or other fluids is pumped, or released, through lumen 43 to selectively inflate and deflate balloon 21. Food and liquid is passed along tube 20 through lumen 42.

As seen in FIG. 1 the balloon 21 is partially inflated when the tube 20 is passed into the stomach 22 through the abdominal wall 23 in a well-known prior art manner as shown, for instance, in the '106 patent, with the aid of an endoscope, to a position as shown in FIG. 1. In this position, the end of the tube has passed through the pylorus 25 into the duodenum 26. The end of tube 20 is held at this location, while the balloon 21 is substantially inflated until it enlarges to contact the wall of the duodenum 26. The endoscope is withdrawn with the tube 20 being held in place by the inflated balloon 21 which extends against the duodenum walls in a fit that retains the tube 21 in position.

Figure 2:
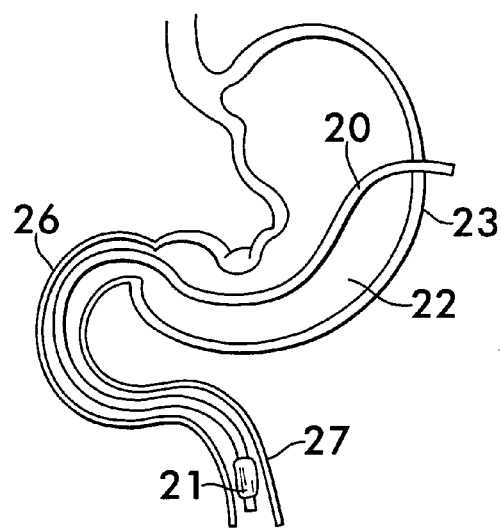
FIG. 2 shows the feeding tube of FIG. 1 with the balloon in the jejunum. It is partially deflated, thus preventing obstruction, but large enough to allow the natural peristaltic action of the small bowel to carry the tube in to the jejunum.
Figure 3:
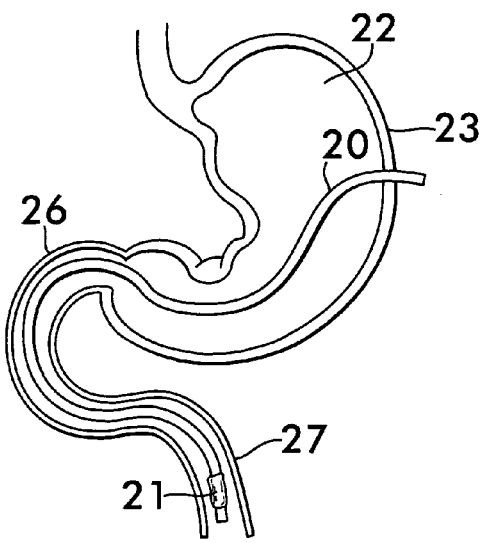
FIG. 3 shows the feeding tube of FIGS. 1 and 2 with the balloon in the jejunum but fully deflated. This is desired after the tube has been carried into the jejunum, thus eliminating any chance of obstruction.
Figure 4:
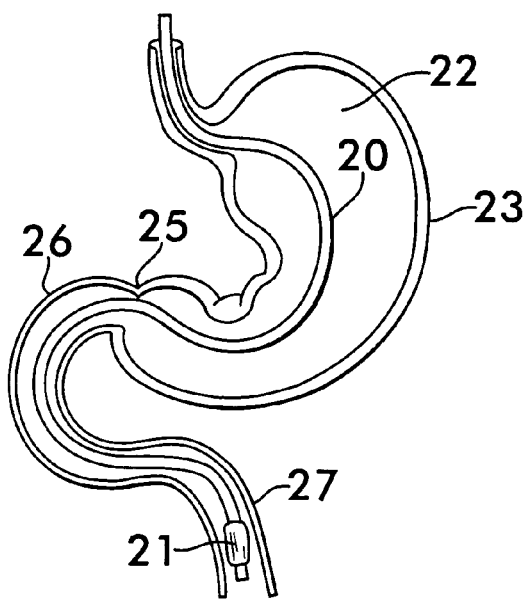
FIG. 4 shows the tube of FIG. 1 through 3 entering the stomach through the esophagus via the nose.

As seen in FIG. 2, the balloon 21 is partially deflated as the tube 20 moves through the duodenum 26 into the jejunum 27. The duodenum considers the balloon as a food bolus and begins its peristaltic action to move the balloon 21 along the duodenum into the jejunum. When the tube reaches the desired end point of the placement in the jejunum, as seen in FIG. 3, the balloon 21 is deflated, either partially or fully, so that no possible blockage can occur.

The balloon 21 is left in a deflated condition during a subsequent withdrawal.

What is claimed is:

1. A method of positioning, in a patient, through the stomach, the distal end of an enteral feeding tube in the jejunum or small bowel of the patient;

the improvement comprising:
 (1) positioning the distal end through the stomach in the duodenum with an endoscope; and then
 (2) inflating a balloon on the distal end of the tube to a size that anchors the tube in place in the duodenum to permit the endoscope to be withdrawn without the tube being pulled back into the stomach; and then
 (3) withdrawing the endoscope from the patient while the tube remains anchored in place in the duodenum by the balloon; and then
 (4) deflating the balloon to a size that allows peristaltic action in the intestines of the patient to act on the balloon to advance the tube from the duodenum into the jejunum of the patient; and then
 (5) further deflating the balloon inside the jejunum to avoid any blockage of the intestines by the balloon while the tube is in the patient.

* * * * *